United States Patent
Huang et al.

(10) Patent No.: US 10,357,525 B2
(45) Date of Patent: Jul. 23, 2019

(54) USE OF A POLYSACCHARIDE MIXTURE FOR TREATING HYPERGLYCEMIA

(71) Applicant: TRINEO BIOTECHNOLOGY CO. LTD, New Taipei (TW)

(72) Inventors: Cheng-Po Huang, Hsinchu (TW); Cheng-Chiu Tsao, Taipei (TW); Chao-hsuan Chang, Taipei (TW); Teng-Hai Chen, Tainan (TW); Li-Ming Huang, Tainan (TW); Chieh-Hung Lin, Tainan (TW)

(73) Assignee: TRINEO BIOTECHNOLOGY CO. LTD, New Taipei ( * ) Notice: Subject to any disclaimer, the term of this patent is extended or adjusted under 35 U.S.C. 154(b) by 0 days.

(21) Appl. No.: 15/609,050

(22) Filed: May 31, 2017

(65) Prior Publication Data

US 2018/0344784 A1   Dec. 6, 2018

(51) Int. Cl.
*A61K 36/074* (2006.01)
*A61K 31/716* (2006.01)
*A61K 45/06* (2006.01)

(52) U.S. Cl.
CPC .......... *A61K 36/074* (2013.01); *A61K 31/716* (2013.01); *A61K 45/06* (2013.01)

(58) Field of Classification Search
CPC ..... A61K 36/074; A61K 45/06; A61K 31/716
See application file for complete search history.

(56) References Cited

U.S. PATENT DOCUMENTS 6,737,065 B2 * 5/2004 Song ............ A61K 36/07
424/195.15

OTHER PUBLICATIONS

Zhang et al., Life Sciences, 2003, 73, p. 2307-2319. (Year: 2003).*
Ellis et al., Diabet. Med., 2011, 28, p. 1176-1181. (Year: 2011).*
Nie et al., Bioactive Carbohydrates and Dietary Fibre, 2013, 1, p. 10-20. (Year: 2013).*

* cited by examiner

*Primary Examiner* — Jonathan S Lau

(57) ABSTRACT

Disclosed herein is a novel use of a polysaccharide mixture for the treatment of hyperglycemia and/or disorders related thereto (e.g., diabetes mellitus). The polysaccharide mixture comprises about 30-50% (wt %) of β(1→3) glucan and β(1→6) glucan, and has a molecular weight of at least 500,000. The polysaccharide mixture may be administered to a subject suffering from hyperglycemia in a dose of about 1 to 1,000 mg/Kg to ameliorate or alleviate symptoms associated with hyperglycemia.

5 Claims, 2 Drawing Sheets

USE OF A POLYSACCHARIDE MIXTURE FOR TREATING HYPERGLYCEMIA

BACKGROUND OF THE INVENTION

1. Field of the Invention

The present disclosure in general relates to a novel use of a polysaccharide mixture for the prophylaxis and/or treatment of hyperglycemia, such as diabetes mellitus.

2. Description of Related Art

Diabetes mellitus (DM) is a condition in which a person's body does not produce enough, or does not properly respond to, insulin. Insulin is a hormone produced in the pancreas that enables cells to absorb glucose to turn it into energy. When insulin production is insufficient or when the body does not properly respond to insulin, glucose accumulates in the blood, which can lead to various complications. While there are several forms of diabetes, three forms are the most recognized: type I diabetes, type II diabetes, and gestational diabetes. Additionally, prediabetes is recognized as preceding diabetes and exists when blood glucose levels that are higher than normal but not yet high enough to be diagnosed as diabetes.

Type I diabetes or insulin-dependent diabetes mellitus (IDDM) is a metabolic disorder caused by destruction of the insulin-producing beta cells in the pancreas, which leads to insulin deficiency and high levels of glucose in plasma. The onset of type I diabetes generally results from an autoimmune etiology; however, idiopathic causes of beta cell destruction can occur for type I. Type I diabetes can affect children or adults, but was traditionally termed "juvenile diabetes" because it represents a majority of the diabetes cases in children.

Type II diabetes or non-insulin-dependent diabetes mellitus (NIDDM) has been found to possess inheritable aspects which can be greatly impacted by external environmental factors. The underlying etiologies of type II diabetes include deficiencies in insulin-producing beta cells; altered response to insulin by muscle, adipose, and liver cells; and abnormalities in the regulating mechanisms responsible for controlling carbohydrate and lipid metabolism following ingestion of food. Modulation in insulin-sensitivity is affected by environmental factors and behaviors, mostly a sedentary lifestyle and obesity. The cellular mechanisms that contribute to modulation of muscle and adipose cell sensitivity to insulin are complex and are not well understood. It is believed that altering insulin signaling pathways, increasing the amount of intracellular fat, and elevating levels of free fatty acids and other adipose tissue products can impact insulin-sensitivity.

Gestational diabetes occurs in pregnant women who have not previously been diagnosed with diabetes but who have high glucose levels during pregnancy. Gestational diabetes affects about 4% of all pregnant women and may precede development of type II diabetes.

If not properly controlled or stabilized, a hyperglycemic state has been associated with comorbidities including cardiovascular disease, vision impairment, various forms of neuropathy and cognitive impairment, stroke, and peripheral vascular disease. The common therapeutic approach, in addition to major modifications in an individual's dietary nutrition and physical activity, includes the use of anti-hyperglycemic drugs and insulin. Since the disease is chronic and progressive, and so far no treatment is able to reverse the progression, and thus there remains in this field a need of an improved medicament for treating conditions, diseases and/or disorders associated with hyperglycemia.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present invention relates to a medicament, which alone or in combination with any blood glucose reduction agent, do effectively reduce the blood glucose level of a hyperglycemia subject. The present invention therefore is useful for treating a disease and/or disorder related to hyperglycemia, which includes, but is not limited to, type I, type II diabetes mellitus, gestational diabetes, other forms of diabetes and/or disorders related thereto.

Accordingly, the first aspect of the present disclosure aims at providing use of a polysaccharide mixture for the manufacture of a medicament suitable for treating conditions related to hyperglycemia. The polysaccharide mixture has a molecular weight of at least 500,000 and about 30-50% (wt %) of $\beta(1\rightarrow 3)$ glucan and $\beta(1\rightarrow 6)$ glucan.

According to embodiments of the present disclosure, the polysaccharide mixture is derived from *Ganoderma lucidum* mycelium.

According to embodiments of the present disclosure, the medicament comprises 1 to 1,000 mg of the polysaccharide mixture; preferably, 10 to 800 mg of the polysaccharide mixture; and more preferably, 50 to 600 mg of the polysaccharide mixture.

According to preferred embodiments of the present disclosure, the medicament is suitable for oral administration.

According to preferred embodiments of the present disclosure, the medicament further includes a blood glucose reduction agent, which may be a glucagon-like peptide 1 (GLP-1) receptor agonist, dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, or $\alpha$-glycosidase inhibitor.

According to some embodiments of the present disclosure, the GLP-1 receptor agonist is liraglutide, exenatide, albiglutide or LY2189265.

According to some embodiments of the present disclosure, the DPP-4 inhibitor is gliptins.

According to some embodiments of the present disclosure, the gliptins is selected from the group consisting of sitagliptin, vildagliptin, saxagliptin, linagliptin, gemigliptin, anagliptin, teneligliptin, alogliptin, trelagliptin, dutogliptin, and omarigliptin.

According to some embodiments of the present disclosure, the insulin analogue is glargine, degludec or detemir.

According to some embodiments of the present disclosure, the biguanide is metformin, phenformin, or bufomin.

According to some embodiments of the present disclosure, the sulfonylurea is glibenclamide, gliclazide, glimepiride, or glipizide.

According to some embodiments of the present disclosure, the TZD is pioglitazone, rosiglitazone, lobeglitazone, ciglitazone, darglitazone, englitazone, netoglitazone, rivoglitazone, or troglitazone.

According to some embodiments of the present disclosure, the SGLT2 inhibitor is dapagliflozin, empagliflozin, canagliflozin, Ipragliflozin, tofogliflozin, sergliflozin etabonate, remogliflozin etabonat, or ertugliflozin.

According to some embodiments of the present disclosure, the α-glycosidase inhibitor is acarbose, miglitose, or voglibose.

The second aspect of the present disclosure aims to provide a method of treating a subject suffering from a disease and/or disorder related to hyperglycemia, which includes but is not limited to, type I, type II diabetes mellitus, gestational diabetes, and other forms of diabetes and/or disorders related thereto. The method comprises the step of, administering to the subject the present polysaccharide mixture described above in a dose of about 1 to 1,000 mg/Kg to ameliorate or alleviate symptoms associated with hyperglycemia.

According to preferred embodiment of the present disclosure, the polysaccharide mixture comprises about 30-50% (wt %) of β(1→3) glucan and β(1→6) glucan, and has a molecular weight of at least 500,000.

According to embodiments of the present disclosure, the polysaccharide mixture is derived from *Ganoderma lucidum* mycelium.

According to preferred embodiment of the present disclosure, the present polysaccharide mixture is administered to the subject orally.

According to preferred embodiment of the present disclosure, the method further includes administering a blood glucose reduction agent to the subject before, together with and/or after administering the present polysaccharide mixture. According to embodiments of the present disclosure, the blood glucose reduction agent may be a glucagon-like peptide 1 (GLP-1) receptor agonist, dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, or α-glycosidase inhibitor.

According to some embodiments of the present disclosure, examples of the GLP-1 receptor agonist include, but are not limited to, liraglutide, exenatide, albiglutide and LY2189265.

According to preferred embodiments of the present disclosure, the DPP-4 inhibitor is gliptin, which may be selected from the group consisting of sitagliptin, vildagliptin, saxagliptin, linagliptin, gemigliptin, anagliptin, teneligliptin, alogliptin, trelagliptin, dutogliptin, and omarigliptin.

According to some embodiments of the present disclosure, the insulin analogue is glargine, degludec or detemir.

According to some embodiments of the present disclosure, the biguanide is metformin, phenformin, or bufomin.

According to some embodiments of the present disclosure, the sulfonylurea is glibenclamide, gliclazide, glimepiride, or glipizide.

According to some embodiments of the present disclosure, the TZD is pioglitazone, rosiglitazone, lobeglitazone, ciglitazone, darglitazone, englitazone, netoglitazone, rivoglitazone, or troglitazone.

According to some embodiments of the present disclosure, the SGLT2 inhibitor is dapagliflozin, empagliflozin, canagliflozin, Ipragliflozin, tofogliflozin, sergliflozin etabonate, remogliflozin etabonat, or ertugliflozin.

According to some embodiments of the present disclosure, the α-glycosidase inhibitor is acarbose, miglitose, or voglibose.

According to preferred embodiment of the present disclosure, the subject is a mammal, preferably a human.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where.

DETAILED DESCRIPTION OF THE INVENTION

Figure 1:
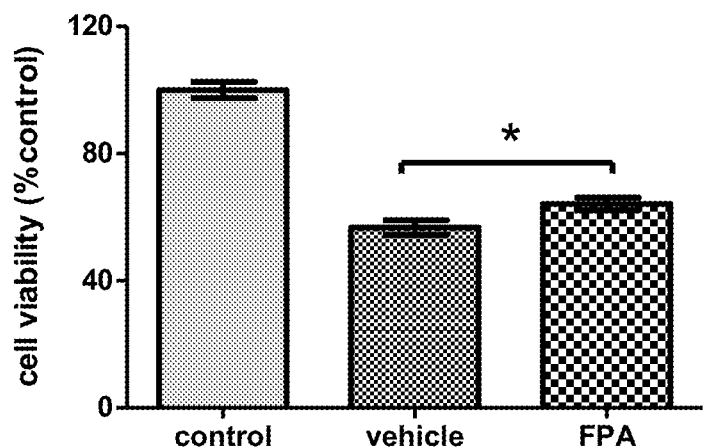
FIG. 1 illustrates the effect of the present polysaccharide mixture on the viability of STZ-treated NIT-1 cells in accordance with one embodiment of the present disclosure.

The detailed description provided below in connection with the appended drawings is intended as a description of the present disclosure and is not intended to represent the only forms in which the present disclosure may be constructed or utilized.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

In the present invention, the term "β(1→3) glucan" includes all glucans having a β(1→3) bond, as well as glucans having a main chain in the form of a β(1→3) glusoside. Similarly, the term "β(1→6) glucan" includes all glucans having a β(1→6) bond, as well as glucans having a main chain in the form of a β(1→6) glusoside. In the present invention, β(1→3) and/or β(1→6) glucans may be obtained from any suitable source, such as plants, mushrooms and/or fungi. According to preferred embodiments of the present disclosure, β(1→3) and/or β(1→6) glucans are prepared from *Gaoderma lucidum* mycelium, for example, by autoclaving the whole fermentation culture of *Gaoderma lucidum*, removing the mycelia by centrifugation, reducing the volume of the broth by concentration until the solid content in the broth reaches about 10%, then lyophilizing the concentrated broth. The thus produced polysaccharide mixture is rich in β(1→3) and/or β(1→6) glucans. According to embodiments of the present disclosure, the polysaccharide mixture comprises about 30-50% (wt %) β(1→3) and/or β(1→6) glucans, and has a molecular weight of at least 500,000.

The term "treatment" as used herein are intended to mean obtaining a desired pharmacological and/or physiologic effect, e.g., inhibiting or suppressing the progressing of diabetes mellitus (DM). The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a is mammal, particularly human; and includes: (1) preventative (e.g., prophylactic), curative or palliative treatment of a disease or condition (e.g., DM) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered," "administering" or "administration" are used interchangeably herein to refer a mode of delivery, including, without limitation, orally, intravenously, intramuscularly, intraperitoneally, intra-arterially, intra-cranially, or subcutaneously administering an agent of the present invention (e.g., the present polysaccharide mixture). In some embodiments, the polysaccharide mixture of the present disclosure are formulated into powders for mixed with suitable carrier (e.g., buffer solution) before use, such as intravenous injection. In other embodiments, the polysaccharide mixture of the present disclosure is formulated into powders with suitable excipients for direct oral ingestion.

The term "an effective amount" as used herein refers to an amount effective, at dosages, and for periods of time necessary, to achieve the desired result with respect to the treatment of a disease resulted from hyperglycemia, such as IDDM, NIDDM, gestational diabetes and etc. For example, in the treatment of IDDM, the present polysaccharide mixture which decrease, prevents, delays or suppresses or arrests any clinical signs of the IDDM would be effective. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) or a ratio of mass of the active agent to body mass, e.g., as milligrams per kilogram (mg/kg). The effective amount may be divided into one, two or more doses in a suitable form to be administered at one, two or more times throughout a designated time period.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "pharmaceutically acceptable" refers to molecules and compositions that do not produce an adverse or undesirable reaction (e.g., toxicity, or allergic reaction) when administered to a subject, such as a human.

The term "excipient" as used herein means any inert substance (such as a powder or liquid) that forms a vehicle/carrier for the active agent. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Detail Description of Preferred Embodiments

The present disclosure is based, at least in part, on the unexpected discovery that a polysaccharide mixture prepared in accordance with examples of the present disclosure may suppress or inhibit the apoptosis of beta cells. Accordingly, the present polysaccharide mixture is useful for the manufacture of a medicament for treating diseases, disorders and/or conditions related to hyperglycemia, which include but are not limited to, IDDM, NIDDM, gestational diabetes, other forms of diabetes and/or disorders related thereto. Optionally, the present polysaccharide mixture can also be administered not only for the treatment of patients, but also in the form of food and drink products such as health food products to healthy persons in a preventive and ameliorative fashion.

The practices of this invention are hereinafter described in detail with respect to use of a polysaccharide mixture having about 30-50% (wt %) of $\beta(1\rightarrow3)$ glucan and $\beta(1\rightarrow6)$ glucan, and a molecular weight of at least 2,500,000. The present polysaccharide mixture is useful for the preparation of a medicament or a health food product for preventing or treating hyperglycemia, or disease caused thereby, in a healthy subject or a patient. Results of the present studies, as described herein below, show that the present polysaccharide mixture possess no cytotoxicity toward normal cells, suppresses apoptosis of beta cells, and reduces the fasting blood glucose level in STZ-induced diabetic animals, thereby suppresses the progression of diabetes in vivo.

The first aspect of the present application is therefore directed to a method of treating a subject having or suffering from diseases, disorders and/or conditions related to hyperglycemia (e.g., IDDM, NIDM, gestational diabetes and etc). The method comprises the step of, administering to the subject in need thereof, an effective amount of the present polysaccharide mixture, which comprises about 30-50% (wt %) of β(1→3) glucan and β(1→6) glucan, and has a molecular weight of at least 500,000, so as to alleviate or ameliorate the symptoms associated with hyperglycemia.

According to preferred embodiments of the present disclosure, the polysaccharide mixture comprises about 30-50% (wt %) of β(1→3) glucan and β(1→6) glucan, such as 30, 31, 32, 33, 34, 35, 36, 37, 38, 39, 40, 41, 42, 43, 44, 45, 46, 47, 48, 49, and 50% of a mixture of β(1→3) glucan and β(1→6) glucan; preferably about 35-45% of β(1→3) glucan and β(1→6) glucan, such as 35, 36, 37, 38, 39, 40, 41, 42, 43, 44, and 45% of a mixture of β(1→3) glucan and β(1→6) glucan; and more preferably, about 40% of β(1→3) glucan and β(1→6) glucan. Further, the polysaccharide mixture has a molecular weight of at least 500,000, such as 500,000, 600,000, 700,000, 800,000, 900,000, 1,000,000, 1,100,000, 1,200,000, 1,300,000, 1,400,000, 1,500,000, 1,600,000, 1,700,000, 1,800,000, 1,900,000, 2,000,000, 2,100,000, 2,200,000, 2,300,000, 2,400,000, 2,500,000, 2,600,000, 2,700,000, 2,800,000, 2,900,000, 3,000,000, 3,100,000, 3,200,000, 3,300,000, 3,400,000, and 3,500,000. Preferably, the polysaccharide mixture has a molecular weight of at least 2,000,000; more preferably, at least 2,500,000.

According to preferred embodiments of the present disclosure, the present polysaccharide mixture is administered to the subject orally, intravenously, or subcutaneously in the amount of 1-1,000 mg/Kg body weight of the subject, preferably in the amount of 10-800 mg/Kg body weight of the subject; more preferably in the amount of 50-600 mg/Kg body weight of the subject.

According to preferred embodiments, the present polysaccharide mixture is administered orally. In this regard, the polysaccharide mixture is preferably in the form of powders that are formulated into tablets or capsules suitable for oral ingestion. Alternatively, the polysaccharide mixture may exist in the form of a solution or a suspension with the polysaccharide mixture homogeneously dispersed therein.

According to optional embodiments, the present polysaccharide mixture may be used in conjugation with another blood glucose reducing agent. The blood glucose reducing agent suitable for use with the present polysaccharide mixture is, for example, glucagon-like peptide 1 (GLP-1) receptor agonist, dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, or α-glycosidase inhibitor.

Suitable examples of the GLP-1 receptor agonist include, but are not limited to, liraglutide, exenatide, albiglutide and LY2189265.

According to some embodiments of the present disclosure, the DPP-4 inhibitor is gliptin, which may be selected from the group consisting of sitagliptin, vildagliptin, saxagliptin, linagliptin, gemigliptin, anagliptin, teneligliptin, alogliptin, trelagliptin, dutogliptin, and omarigliptin.

Non-limiting examples of the insulin analogue include but are not limited to, glargine, degludec and detemir.

Non-limiting examples of the biguanide include, but are not limited to, metformin, phenformin, and bufomin.

Non-limiting examples of the sulfonylurea include, but are not limited to, glibenclamide, gliclazide, glimepiride, and glipizide.

According to some embodiments of the present disclosure, the TZD is pioglitazone, rosiglitazone, lobeglitazone, ciglitazone, darglitazone, englitazone, netoglitazone, rivoglitazone, or troglitazone.

Non-limiting examples of the SGLT2 inhibitor include, but are not limited to, dapagliflozin, empagliflozin, canagliflozin, Ipragliflozin, tofogliflozin, to sergliflozin etabonate, remogliflozin etabonat, and ertugliflozin.

Non-limiting examples of the α-glycosidase inhibitor include, but are not limited to, acarbose, miglitose, and voglibose.

The second aspect of the present application is directed to a medicament for treating diseases, disorders and/or conditions related to hyperglycemia (e.g., IDDM, NIDM, gestational diabetes and etc). The medicament comprises an effective amount of the present polysaccharide mixture, and a pharmaceutically acceptable excipient.

According to some embodiments, the present polysaccharide mixture comprises about 30-50% (wt %) of β(1→3) glucan and β(1→6) glucan, and has a molecular weight of at least 500,000. Preferably, the present polysaccharide mixture comprises about 40% of β(1→3) glucan and β(1→6) glucan, and has a molecular weight of at least 2,500,000.

Generally, the present polysaccharide mixture is present in the medicament at a level of about 0.01% to 99.9% by weight, based on the total weight of the medicament. In some embodiments, the present polysaccharide mixture is present at a level of at least 0.1% by weight, based on the total weight of the medicament. In certain embodiments, the present polysaccharide mixture is present at a level of at least 5% by weight, based on the total weight of the medicament. In still other embodiments, the present polysaccharide mixture is present at a level of at least 10% by weight, based on the total weight of the medicament. In still yet other embodiments, the present polysaccharide mixture is present at a level of at least 25% by weight, based on the total weight of the medicament.

According to embodiments of the present disclosure, each medicaments comprises 1 to 1,000 mg of the polysaccharide mixture; preferably, 10 to 800 mg of the polysaccharide mixture; and more preferably, 50 to 600 mg of the polysaccharide mixture.

In some embodiments, the medicament of this invention further includes an agent (e.g., a blood glucose reduction agent) known to alleviate or ameliorate hyperglycemia condition. Examples of such agent include, and are not limited to, glucagon-like peptide 1 (GLP-1) receptor agonist, dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, and α-glycosidase inhibitor.

Suitable examples of the GLP-1 receptor agonist include, but are not limited to, liraglutide, exenatide, albiglutide and LY2189265.

According to some embodiments of the present disclosure, the DPP-4 is inhibitor is gliptin, which may be selected from the group consisting of sitagliptin, vildagliptin, saxagliptin, linagliptin, gemigliptin, anagliptin, teneligliptin, alogliptin, trelagliptin, dutogliptin, and omarigliptin.

Non-limiting examples of the insulin analogue include but are not limited to, glargine, degludec and detemir.

Non-limiting examples of the biguanide include, but are not limited to, metformin, phenformin, and bufomin.

Non-limiting examples of the sulfonylurea include, but are not limited to, glibenclamide, gliclazide, glimepiride, and glipizide.

According to some embodiments of the present disclosure, the TZD is pioglitazone, rosiglitazone, lobeglitazone, ciglitazone, darglitazone, englitazone, netoglitazone, rivoglitazone, or troglitazone.

Non-limiting examples of the SGLT2 inhibitor include, but are not limited to, dapagliflozin, empagliflozin, canagliflozin, Ipragliflozin, tofogliflozin, sergliflozin etabonate, remogliflozin etabonat, and ertugliflozin.

Non-limiting examples of the α-glycosidase inhibitor include, but are not limited to, acarbose, miglitose, and voglibose.

In preferred example, metformin is administered concurrently with the present polysaccharide mixture.

Pharmaceutically acceptable excipients are those that are compatible with other ingredients in the formulation and biologically acceptable.

The medicament may comprise different types of excipients depending on the intended routes of administration. The present composition may be administered intraveneously, intradermally, intraarterially, intraperitoneally, intralesionally, intracranially, intranasally, intrapleurally, intratracheally, intrarectally, topically, intramuscularly, subcutaneoustly, intravesicularlly, intrapericardially, intraocularally, orally, topically, locally, injection, inhalation, infusion, localized perfusion, in any suitable forms such as powders, creams, liquids, aerosols and etc.

The actual dosage of the medicament may be determined by the attending physician based on the physical and physiological factors of the subject, these factors include, but are not limited to, age, gender, body weight, the disease to be treated, severity of the condition, previous history, the presence of other medications, the route of administration and etc. According to non-limiting examples of the present disclosure, each dosage will give rise to 1-1,000 mg the per Kg body weight per administration, such as 1, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, and 1,000 mg the present polysaccharide mixture per Kg body weight per administration; preferably, 10-800 mg the present polysaccharide mixture per Kg body weight per administration, such as 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, and 800 mg the present polysaccharide mixture per Kg body weight per administration; more preferably in the amount of 50-600 mg the present polysaccharide mixture per Kg body weight per administration, such as, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, and 600 mg the present polysaccharide mixture per Kg body weight per administration.

The medicament containing the present polysaccharide mixturemay be in a form suitable for oral use, for example, as tablets, lozenges, aqueous or oily suspensions, dispersible powders or granules, emulsions, hard or soft capsules, or syrups or elixirs. Medicaments intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the present polysaccharide mixture and non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

The medicaments of the present invention may be in the form of an oil-in-water emulsion. The oily phase may be a vegetable oil, for example olive oil or peanut oil, or a mineral oil, for example liquid paraffin or polysaccharide mixture s of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a preservative, and flavouring and colouring agents.

The medicaments may be in the form of a sterile injectable aqueous or oleagenous suspension. This suspension may be formulated according to the is known art using suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringers solution and isotonic sodium chloride solution. Co-solvents such as ethanol, propylene glycol or polyethylene glycols may also be used.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLES

Materials and Methods

Submerged culture of G. lucidum. The culture medium useful for cultivating G. lucidum was prepared by dissolving the following ingredients in water, so that each liter of the medium contained 60 glucose, 15 g sucrose, 3 g peptone, 18 g yeast extract, and 0.6 g potassium dihydrogen phosphate (pH <4.5).

G. lucidum mycelium (3 Kg) was then added to the designated amount of autoclaved culture medium, and cultivated for desired period of time with a constant agitation at a speed of 100-150±10 rpm. The culture was maintained at a temperature of 28±1° C., and a pressure of about 0.6±0.05 Kg/cm$^2$.

Content of polysaccharides. The polysaccharide mixture was dispersed in NaOH (0.5M) and stirred at ambient temperature until completely dissolved. Then, the content of the polysaccharide mixture was determined using a phenol-sulfuric acid method, and glucose was used as a standard.

Sugar composition of polysaccharides. The polysaccharide (1-5 mg) was methanolyzed under vaccum in 1 mL of anhydride HCI (2M) in absolute methanol in a sealed hydrolytic tube at 80° C. for 12 hr. Next, the reagent was removed by evaporation, and the methyl glycosides generated during methanolysis was further analyzed with trifluoroacetic acid (TFA, 2M) at 100° C. for 1.5 hr. After removal of TFA be repeated evaporation under vacuum with HPLC grade distilled water, the sugars in the hydrolysis were analyzed by high performance anion-exchange chromatography with pulsed amperometric detection (HPAEC-PAD).

Cells. Cell line used in the present study was pancreatic beta cell line NIT-1 (Belgian Ceramic Research Centre, BCRC). NIT-1 cells were cultured and maintained in Ham's F12K medium with 2 mM L-glutamine adjusted to contain 1.5 g/L sodium bicarbonate, 90%; heat-inactivated dialyzed fetal bovine serum(FBS), 10%; 100 units/mL penicillin G, 100 units/mL streptomycin (pH 7.4) and 1% non-essential amino acids(NEAA). were maintained in humidified environment comprising 5%$CO_2$/95% air at 37° C.

Animals. Balb/c mice (7 weeks old) were obtained from the National Laboratory Animal Center (Taipei, Taiwan) and were kept in a pathogen-free facility with controlled temperature (20-24° C.), humidity (50-80%) and a 12 h/12 h light/dark cycle (light on at 7:00 a.m.) with food and water provided ad libitum. Experimental procedures for handling the mice complied with relevant regulations set forth in "Guide for the Care and Use of Laboratory Animals: Eighth Edition" (National Academies Press, Washington, D.C., 2011) in AAALAC-accredited laboratory animal facility.

STZ-induced apoptosis and treatment

NIT-1 cells were seeded into 96-well plates at a density of $1.0 \times 10^5$ cells per well and cultured in their normal growth media overnight. Next day, cells were incubated in the presence of streptozotocin (STZ) (8 µM) and the polysaccharide mixture (abbreviated as "FPA", 100 µg/mL) of the present invention for 24 hrs, then cell viability was determined by MTT assay.

MTT assay

MTT is a colorimetric assay that measures the activity of enzymes (i.e., reductase) that reduce (3-(4,5-dimethylthiazol-2yl)-2,5-diphenyltetrazoliumbromide (MTT), a yellow tetrazole, to purple formazan, in living cells. This reduction only takes place when cells are alive; hence MTT assay is generally used to assess the viability is and proliferation of cells. Briefly, MTT reagent (10 µL) was added to each well and the reaction was allowed to proceed for 3 hours before being terminated by the addition of 500 µL of isopropanol. The absorbance of the solution at 570 nm was measured by spectrophotometer.

STZ-induced diabetic mice and Treatment

Wide-type male Balb/c mice (about 7 weeks old) were first given the present polysaccharide mixture (600 mg/Kg/day) for 9 days, then were rendered diabetic by two intraperitoneal injections of STZ, in which the first STZ injection was given on day 10 at the dose of 150 mg/Kg, and the second STZ injection was given on day 17 at the dose of 200 mg/Kg. On day 18, fluorescent marker (Annexcin-Vivo™ 750, Perkin Elmer) (100 µL/mouse) was injected through the tail vein, and the mice were then subject to live imagine analysis using FMT 4000 (Perkin Elmer). Animals were then sacrificed and their pancreatic tissues were taken out and analyzed by Hematoxylin and Eosin (H&E) Staining.

Control animals were given the treatment of distilled water instead of the present polysaccharide mixture. Fasting blood glucose levels were determined on days 1, and 25.

Hematoxylin and Eosin (H&E) Staining. H&E staining was used to show apoptosis of pancreatic tissues in mice with hyperglycemia in comparison with control and the present polysaccharide mixture treated mice. All staining was performed on tissues that were collected at the end of the experiment in accordance with standard procedures.

Example 1

Preparation and Characterization of the Present Polysaccharide Mixture 1.1 Submerged Cultivation Products of Ganoderma lucidum Mycelium To produce the desired polysaccharide mixture, G. lucidum mycelium (3 Kg) was cultivated sequentially in 50, 500 and 5,000 liters autoclaved culture medium for 3, 3, and 12-14 days, respectively. Then, the whole fermentation cultures were harvested and autoclaved, and the mycelia removed by centrifugation. The broth was collected and reduced by concentration until the solid content was about 10%, then freeze-dried to produce a polysaccharide mixture (about 90 Kg).

1.2 Characterization of the Polysaccharide Mixture of Example 1.1

The content and sugar composition of the polysaccharide mixture of example 1.1 was determined by the procedures as described in the "Materials and Methods" section. Results indicated that the polysaccharide mixture of example 1.1 had a molecular weight exceeding 2,500,000, and was composed of about 40% of β(1→3) glucan and β(1→6) glucan.

Example 2

Effects of the Polysaccharide Mixture of Example 1 on Hyperglycemia 2.1 STZ-Induced Apoptosis in NIT-Cells NIT-1 cells are pancreatic beta cell lines established from transgenic mice spontaneously developing beta-cell adenoma, thus, NIT-1 cells are suitable for hyperglycemia study for they are not responsive to glucose in the physiological range. Prior studies indicated that low dose STZ treatment may cause beta cell apoptosis. Accordingly, the protective effect of the present polysaccharide mixture of example 1 on STZ-treated NIT-1 cells was evaluated by MTT assay. Result is illustrated in FIG. 1.

As evidenced in FIG. 1, significant portion of NIT-1 cells (about 60%) died after STZ (8 µM) treatment, however, if the present polysaccharide mixture (100 µg/mL, abbreviated as "FPA") was administered to the NIT-1 cells before STZ was administered, then the survival number of NIT-1 cell increased slightly, which is a clear indication that the present polysaccharide mixture may protect NIT-1 cells from STZ-induced apoptosis.

2.2 STZ-Induced Diabetic Mice

Figure 2:
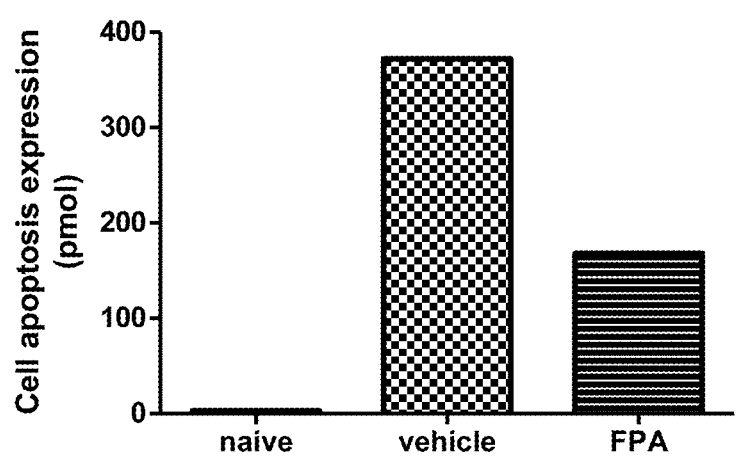
FIG. 2 illustrates the effect of the present polysaccharide mixture on the apoptotic death of pancreatic tissues of STZ-induced diabetic mice in accordance with one embodiment of the present disclosure.
Figure 3:
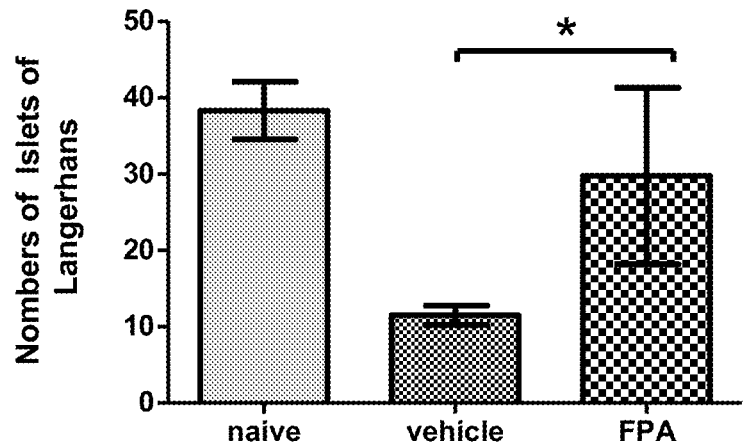
FIG. 3 is a bar graph depicting the effect of the present polysaccharide mixture on the number of islets of Langerhans in STZ-induced diabetic mice in accordance with one embodiment of the present disclosure.
Figure 4:
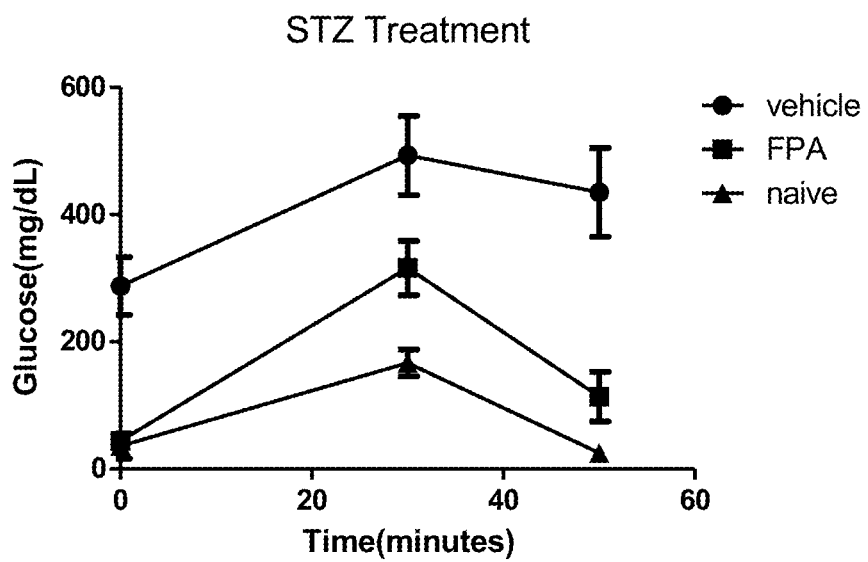
FIG. 4 depicts the effect of the present polysaccharide mixture on the fasting blood glucose level in STZ-induced diabetic mice in accordance with one embodiment of the present disclosure.

STZ-induced diabetic mice were induced and treated in accordance with the steps described in the "Materials and Methods" section, and results are illustrated in FIGS. 2 to 4.

According to data in FIG. 2, STZ treatment resulted in significant apoptotic death in pancreatic cells as determined by live fluorescence imaging, to and the STZ-induced apoptotic death was suppressed by pre-treating the mice with the present polysaccharide mixture (FPA, 600 mg/Kg).

The afore-mentioned results were confirmed by histological analysis, in which 4-6 um tissue sections were prepared from pancreas of all mice at the end of the experiment. These tissues were stained with H&E to show the remaining survived islets of Langerhans, in which intact islets of Langerhans were observed in both the control mice and the mice treated with the present polysaccharide mixture, but not in STZ-treated mice (data not shown).

The same pancreatic tissue were also subject to microscopy analysis, in which the number of survived islets of Langerhans were quantified and results were illustrated in FIG. 3. In FIG. 3, the number of islets of Langerhans decreased significantly after STZ-treatment (FIG. 3, naïve vs vehicle), and such decrease was suppressed by the treatment of the polysaccharide mixture (FIG. 3, vehicle vs FPA).

2.3 Glucose Level

The result in FIG. 3 is consistent with the findings in FIGS. 1 and 2 that the present polysaccharide mixture may suppress or inhibit the apoptosis of pancreatic cells. In the present example, the effect of the present polysaccharide mixture on fasting blood glucose level was investigated.

Briefly, mice were fasted for 16-18 hrs before subjecting to blood analysis. On the day of the experiment, blood samples were taken at time 0, then each mice were orally given dextrose solution (1 g/Kg), then blood samples were taken respectively at 30 and 150 mines. Results are depicted in FIG. 4.

As expected, the control naïve animals exhibited the lowest blood glucose level, while STZ-treated mice exhibited the highest blood glucose level. Treatment with the present polysaccharide mixture could successfully reduce the elevated blood glucose level down to the level that was close to that of the control animals.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method for the prophylaxis and/or treatment of type II diabetes in a subject comprising administering to the subject a dipeptidyl peptidase-4 (DPP-4) inhibitor and a polysaccharide mixture; wherein the DPP-4 inhibitor is gliptin, and the polysaccharide mixture is derived from *Ganoderma lucidum* mycelium and has a molecular weight of at least 2,500,000 and about 40% (wt %) of β (1→3) glucan and β (1→6) glucan, and the polysaccharide mixture is administered in an amount of about 1 to 1,000 mg/Kg to ameliorate or alleviate symptoms associated with type II diabetes.

2. The method of claim 1, wherein the gliptin is selected from the group consisting of sitagliptin, vildagliptin, saxagliptin, linagliptin, gemigliptin, anagliptin, teneligliptin, alogliptin, trelagliptin, dutogliptin, and omarigliptin.

3. The method of claim 1, wherein the polysaccharide mixture is administered orally, intravenously, intramuscularly, subcutaneously, transmucosally, or intrarectally.

4. The method of claim 1, wherein the polysaccharide mixture is administered to the subject in the amount of about 10 to 800 mg/Kg.

5. The method of claim 1, wherein the subject is a human.

* * * * *